United States Patent
Zhou (10) Patent No.: US 8,784,357 B2
(45) Date of Patent: Jul. 22, 2014

(54) PHACOEMULSIFICATION HAND PIECE WITH TWO INDEPENDENT TRANSDUCERS

(75) Inventor: Jiansheng Zhou, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 552 days.

(21) Appl. No.: 12/882,243

(22) Filed: Sep. 15, 2010

(65) Prior Publication Data

US 2012/0065578 A1    Mar. 15, 2012

(51) Int. Cl.
*A61B 17/20* (2006.01)

(52) U.S. Cl.
USPC .............................. 604/22; 606/166; 606/169

(58) Field of Classification Search
USPC .................................. 604/22; 606/166, 169
See application file for complete search history.

(56) References Cited

U.S. PATENT DOCUMENTS

| | | |
|---|---|---|
| 3,526,219 A | 9/1970 | Balamuth |
| 3,589,363 A | 6/1971 | Banko |
| 3,601,126 A | 8/1971 | Estes et al. |
| 3,693,613 A | 9/1972 | Kelman |
| 3,812,855 A | 5/1974 | Banko |
| 3,812,858 A | 5/1974 | Oringer |
| 3,857,387 A | 12/1974 | Shock |
| 3,902,495 A | 9/1975 | Weiss et al. |
| 3,930,505 A | 1/1976 | Wallach |
| 3,942,519 A | 3/1976 | Shock |
| 3,952,732 A | 4/1976 | Shock |
| 3,956,826 A | 5/1976 | Perdreaux, Jr. |
| 3,964,487 A | 6/1976 | Judson |
| 3,990,452 A | 11/1976 | Murry et al. |
| 4,024,467 A | 5/1977 | Andrews et al. |
| 4,024,866 A | 5/1977 | Wallach |
| 4,114,623 A | 9/1978 | Meinke et al. |
| 4,126,137 A | 11/1978 | Archibald |
| 4,156,187 A | 5/1979 | Murry et al. |
| 4,168,707 A | 9/1979 | Douvas et al. |
| 4,184,510 A | 1/1980 | Murry et al. |
| 4,223,676 A | 9/1980 | Wuchinich |

(Continued)

FOREIGN PATENT DOCUMENTS

| | | |
|---|---|---|
| EP | 359217 | 3/1990 |
| JP | 09009656 | 10/1997 |

(Continued)

OTHER PUBLICATIONS

Shuyu, Lin. "Sandwiched Piezoelectric Ultrasonic Transducers of Longitudinal-Torsional Compound Vibrational Modes." IEEE Transactions of Ultrasonics, Ferroelectrics and Frequency Control, Nov. 1997, pp. 1189-1197.

(Continued)

*Primary Examiner* — Emily Schmidt
(74) *Attorney, Agent, or Firm* — Kenneth D. Bassinger (57) ABSTRACT

An ophthalmic surgical hand piece has a horn and two transducers. The horn has a central axis. A flange having a generally flat surface is coupled to the horn. The flange extends radially from the horn and generally perpendicular to the central axis. A first ear having a generally flat surface is coupled to the horn. The first ear extends from the horn such that the generally flat surface of the first ear is generally perpendicular to the generally flat surface of the flange. A first transducer is held against the flange, and a second transducer held against the ear.

12 Claims, 5 Drawing Sheets

(56) References Cited

U.S. PATENT DOCUMENTS

| | | |
|---|---|---|
| 4,246,902 A | 1/1981 | Martinez |
| 4,248,232 A | 2/1981 | Engelbrecht et al. |
| 4,406,284 A | 9/1983 | Banko |
| 4,417,578 A | 11/1983 | Banko |
| 4,493,694 A | 1/1985 | Wuchinich |
| 4,496,342 A | 1/1985 | Banko |
| 4,504,264 A | 3/1985 | Kelman |
| 4,508,532 A | 4/1985 | Drews et al. |
| 4,515,583 A | 5/1985 | Sorich |
| 4,589,415 A | 5/1986 | Haaga |
| 4,590,935 A | 5/1986 | Ranalli |
| 4,609,368 A | 9/1986 | Dotson, Jr. |
| 4,651,280 A | 3/1987 | Chang et al. |
| 4,658,819 A | 4/1987 | Harris et al. |
| 4,705,500 A | 11/1987 | Reimels et al. |
| 4,712,544 A | 12/1987 | Ensslin |
| 4,739,759 A | 4/1988 | Rexroth et al. |
| 4,750,488 A | 6/1988 | Wuchinich et al. |
| 4,770,654 A | 9/1988 | Rogers et al. |
| 4,793,346 A | 12/1988 | Mindich |
| 4,827,911 A | 5/1989 | Broadwin et al. |
| 4,869,715 A | 9/1989 | Sherburne |
| 4,922,902 A | 5/1990 | Wuchinich et al. |
| 4,961,424 A | 10/1990 | Kubota et al. |
| 4,969,885 A | 11/1990 | Farin |
| 4,989,583 A | 2/1991 | Hood |
| 4,989,588 A | 2/1991 | Kubota et al. |
| 5,026,387 A | 6/1991 | Thomas |
| 5,116,343 A | 5/1992 | Ames et al. |
| 5,139,509 A | 8/1992 | Fischer et al. |
| 5,151,085 A | 9/1992 | Sakurai et al. |
| 5,154,694 A | 10/1992 | Kelman |
| 5,154,696 A | 10/1992 | Shearing |
| 5,160,317 A | 11/1992 | Costin |
| 5,180,363 A | 1/1993 | Idemoto et al. |
| 5,188,102 A | 2/1993 | Idemoto et al. |
| 5,205,817 A | 4/1993 | Idemoto et al. |
| 5,222,959 A | 6/1993 | Anis |
| 5,242,385 A | 9/1993 | Strukel |
| 5,279,547 A | 1/1994 | Costin |
| 5,304,115 A | 4/1994 | Pflueger et al. |
| 5,342,293 A | 8/1994 | Zanger |
| 5,359,996 A | 11/1994 | Hood |
| 5,431,664 A | 7/1995 | Ureche et al. |
| 5,520,633 A | 5/1996 | Costin |
| 5,569,188 A | 10/1996 | Mackool |
| 5,591,127 A | 1/1997 | Barwick, Jr. et al. |
| 5,676,649 A | 10/1997 | Boukhny et al. |
| 5,700,240 A | 12/1997 | Barwick, Jr. et al. |
| 5,722,945 A | 3/1998 | Anis et al. |
| 5,733,256 A | 3/1998 | Costin |
| 5,766,146 A | 6/1998 | Barwick, Jr. |
| 5,808,396 A | 9/1998 | Boukhny |
| 5,865,790 A | 2/1999 | Bair |
| 6,027,515 A | 2/2000 | Cimino |
| 6,028,387 A | 2/2000 | Boukhny |
| 6,077,285 A | 6/2000 | Boukhny |
| 6,083,193 A | 7/2000 | Kadziauskas et al. |
| 6,175,180 B1 | 1/2001 | Angelini et al. |
| 6,179,808 B1 | 1/2001 | Boukhny et al. |
| 6,193,683 B1 | 2/2001 | Ludin et al. |
| 6,261,283 B1 | 7/2001 | Morgan et al. |
| 6,261,297 B1 | 7/2001 | Kadziauskas et al. |
| 6,283,974 B1 | 9/2001 | Alexander |
| 6,315,755 B1 | 11/2001 | Sussman |
| 6,402,769 B1 | 6/2002 | Boukhny |
| 6,629,948 B2 | 10/2003 | Rockley |
| 6,699,212 B1 | 3/2004 | Kadziauskas |
| 6,780,165 B2 | 8/2004 | Kadziauskas et al. |
| 7,374,552 B2 | 5/2008 | Wuchinich |
| 7,651,490 B2 | 1/2010 | Boukhny et al. |
| 2001/0001123 A1 | 5/2001 | Madan et al. |
| 2001/0011176 A1 | 8/2001 | Boukhny et al. |
| 2003/0045887 A1 | 3/2003 | Sakurai et al. |
| 2003/0164659 A1 | 9/2003 | Iino et al. |
| 2004/0092800 A1 | 5/2004 | Mackool |
| 2004/0092922 A1 | 5/2004 | Kadziauskas et al. |
| 2004/0215127 A1 | 10/2004 | Kadziauskas et al. |
| 2006/0036180 A1* | 2/2006 | Boukhny et al. ............ 600/471 |
| 2006/0041200 A1 | 2/2006 | Dotter et al. |

FOREIGN PATENT DOCUMENTS

| | | |
|---|---|---|
| JP | 2003033364 | 4/2003 |
| WO | WO 8705793 | 10/1987 |
| WO | WO 92/07622 | 5/1992 |
| WO | WO 99/45868 | 9/1999 |
| WO | WO 01/41672 | 6/2001 |
| WO | WO 2004/080505 | 9/2004 |

OTHER PUBLICATIONS

Jiromaru Tsujino, "Ultrasonic Motor Using A One-Dimensional Longitudinal-Torsional Vibration Converter With Diagonal Slits", Smart Mater. Struct. 7 (1998) 345-351.

* cited by examiner

PHACOEMULSIFICATION HAND PIECE WITH TWO INDEPENDENT TRANSDUCERS

BACKGROUND OF THE INVENTION

The present invention relates to phacoemulsification surgery and more particularly to phacoemulsification hand piece that is capable of imparting both longitudinal and torsional motion to a cutting tip.

The human eye functions to provide vision by transmitting light through a clear outer portion called the cornea, and focusing the image by way of a crystalline lens onto a retina. The quality of the focused image depends on many factors including the size and shape of the eye, and the transparency of the cornea and the lens. When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. A typical surgical hand piece suitable for phacoemulsification procedures consists of an ultrasonically driven phacoemulsification hand piece, an attached hollow cutting needle surrounded by an irrigating sleeve, and an electronic control console. The hand piece assembly is attached to the control console by an electric cable and flexible tubing. Through the electric cable, the console varies the power level transmitted by the hand piece to the attached cutting needle. The flexible tubing supplies irrigation fluid to the surgical site and draws aspiration fluid from the eye through the hand piece assembly.

The operative part in a typical hand piece is a centrally located, hollow resonating bar or horn directly attached to a set of piezoelectric crystals. The crystals supply the required ultrasonic vibration needed to drive both the horn and the attached cutting needle during phacoemulsification, and are controlled by the console. The crystal/horn assembly is suspended within the hollow body or shell of the hand piece by flexible mountings. The hand piece body terminates in a reduced diameter portion or nosecone at the body's distal end. Typically, the nosecone is externally threaded to accept the hollow irrigation sleeve, which surrounds most of the length of the cutting needle. Likewise, the horn bore is internally threaded at its distal end to receive the external threads of the cutting tip. The irrigation sleeve also has an internally threaded bore that is screwed onto the external threads of the nosecone. The cutting needle is adjusted so that its tip projects only a predetermined amount past the open end of the irrigating sleeve.

During the phacoemulsification procedure, the tip of the cutting needle and the end of the irrigation sleeve are inserted into the anterior capsule of the eye through a small incision in the outer tissue of the eye. The surgeon brings the tip of the cutting needle into contact with the lens of the eye, so that the vibrating tip fragments the lens. The resulting fragments are aspirated out of the eye through the interior bore of the cutting needle, along with irrigation solution provided to the eye during the procedure, and into a waste reservoir.

Power is applied to the hand piece to vibrate the cutting needle. In general, the amplitude of needle movement (or vibration) is proportional to the power applied. In conventional phacoemulsification systems, the needle vibrates back and forth producing a longitudinal needle stroke. In improved systems, the needle may be caused to vibrate in a twisting or torsional motion. One way to achieve twisting or torsional motion is described in U.S. Pat. No. 7,651,490. Twisting or torsional motion of the cutting tip has proven a very effective way of removing lens material. Twisting or torsional movement of the cutting tip avoids repulsion that can occur with traditional longitudinal movement of the cutting tip and leads to more effective lens removal. In other instances, longitudinal motion may be used to clear an occluded tip by pushing the lens material away from the tip. As such, during cataract surgery both longitudinal and torsional or twisting motion may be desirable depending on the circumstances. Moreover, it may also be desirable to have both types of motion at the cutting tip simultaneously.

SUMMARY OF THE INVENTION

In one embodiment consistent with the principles of the present invention, the present invention is an ophthalmic surgical hand piece having a horn and two transducers. The horn has a central axis. A flange having a generally flat surface is coupled to the horn. The flange extends radially from the horn and generally perpendicular to the central axis. A first ear having a generally flat surface is coupled to the horn. The first ear extends from the horn such that the generally flat surface of the first ear is generally perpendicular to the generally flat surface of the flange. A first transducer is held against the flange, and a second transducer held against the ear.

In another embodiment consistent with the principles of the present invention, the present invention is an ophthalmic surgical hand piece having a horn with a central axis. A flange is coupled to the horn. The flange has a first surface generally perpendicular to the central axis of the horn and a second surface generally parallel to the central axis of the horn. A first ear is coupled to the horn. The first ear has a generally flat surface extending from the horn such that the generally flat surface of the first ear is generally parallel to the second surface of the flange. A first transducer is held against the first surface of the flange. A second transducer held between the first ear and the second surface of the flange.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
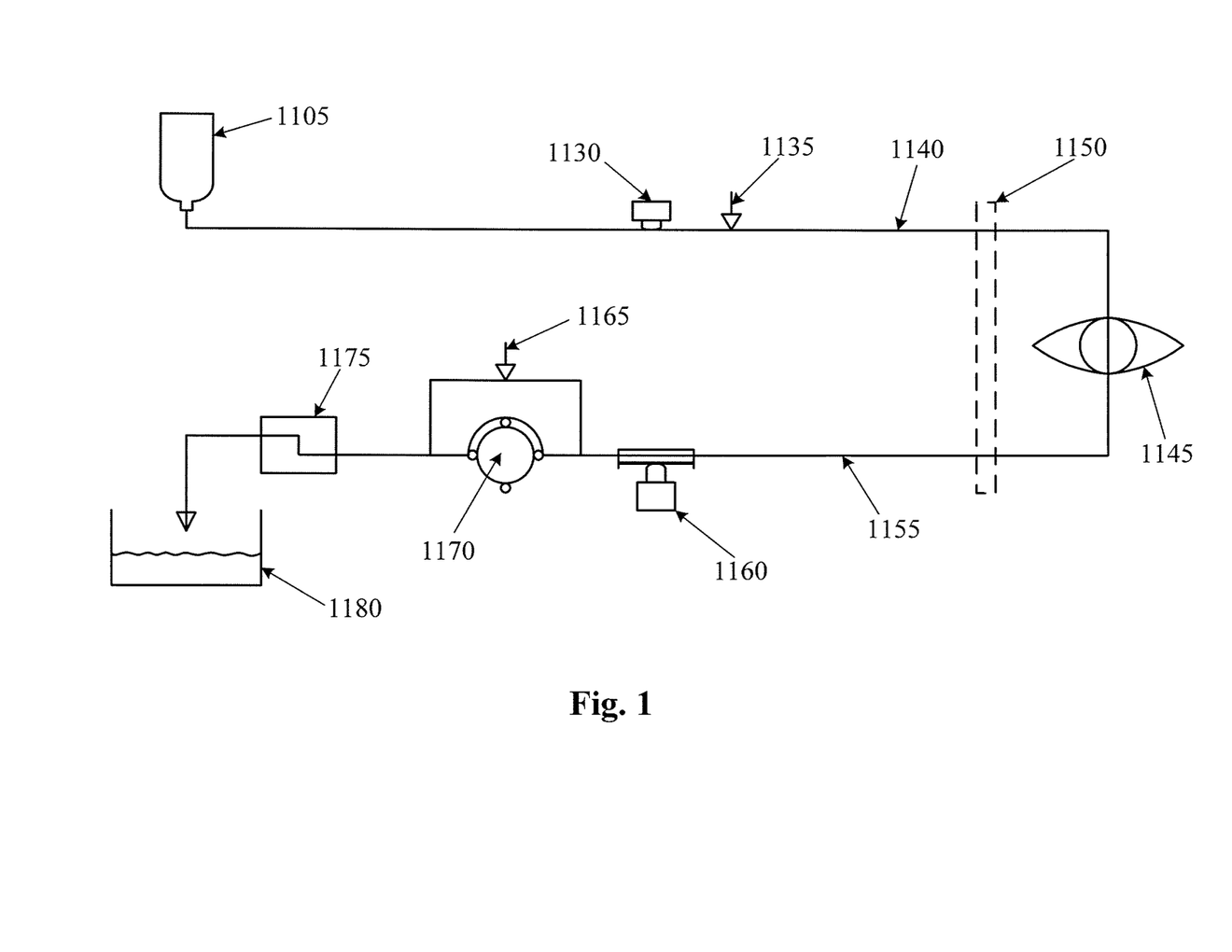
FIG. 1 is a diagram of the components in the fluid path of a phacoemulsification system.

In one embodiment of the present invention, FIG. 1 is a diagram of the components in the fluid path of a phacoemulsification system. FIG. 1 depicts the fluid path through the eye 1145 during cataract surgery. The components include an irrigation fluid source 1105, an irrigation pressure sensor 1130, an irrigation valve 1135, an irrigation line 1140, a hand piece 1150, an aspiration line 1155, an aspiration pressure sensor 1160, a vent valve 1165, a pump 1170, a reservoir 1175 and a drain bag 1180. The irrigation line 1140 provides irrigation fluid to the eye 1145 during cataract surgery. The aspiration line 1155 removes fluid and emulsified lens particles from the eye during cataract surgery.

When irrigation fluid exits irrigation fluid source 1105, it travels through irrigation line 1140 and into the eye 1145. An irrigation pressure sensor 1130 measures the pressure of the irrigation fluid in irrigation line 1140. An optional irrigation valve 1135 is also provided for on/off control of irrigation. Irrigation pressure sensor 1130 is implemented by any of a number of commercially available fluid pressure sensors and can be located anywhere in the irrigation fluid path (anywhere between the irrigation source 1105 and the eye 1145).

A hand piece 1150 is placed in the eye 1145 during a phacoemulsification procedure. The hand piece 1150 has a hollow needle (as seen in FIG. 2) that is ultrasonically vibrated in the eye to break up the diseased lens. A sleeve located around the needle provides irrigation fluid from irrigation line 1140. The irrigation fluid passes through the space between the outside of the needle and the inside of the sleeve (as more clearly shown in FIG. 2A). Fluid and lens particles are aspirated through the hollow needle. In this manner, the interior passage of the hollow needle is fluidly coupled to aspiration line 1155. Pump 1170 draws the aspirated fluid from the eye 1145. An aspiration pressure sensor 1160 measures the pressure in the aspiration line. An optional vent valve can be used to vent the vacuum created by pump 1170. The aspirated fluid passes through reservoir 1175 and into drain bag 1180.

Figure 2A:
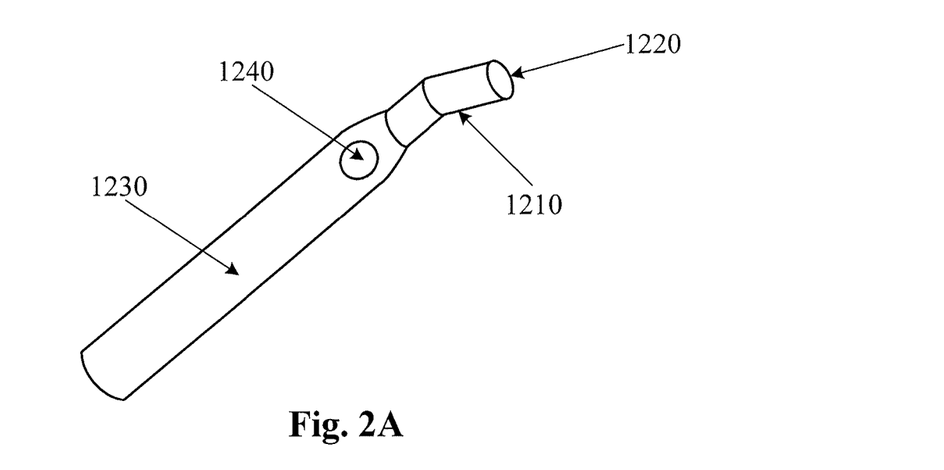
FIGS. 2A-2D are perspective views of the distal end of a phacoemulsification needle and irrigation sleeve according to the principles of the present invention.
Figure 2B:
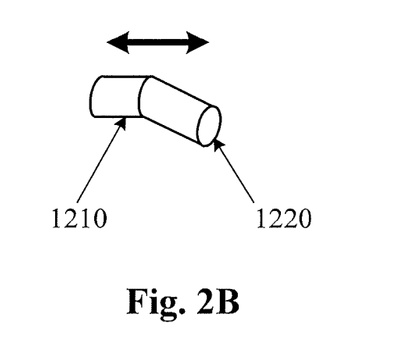
Figure 2C:
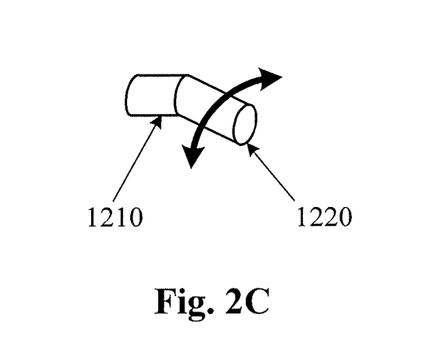
Figure 2D:
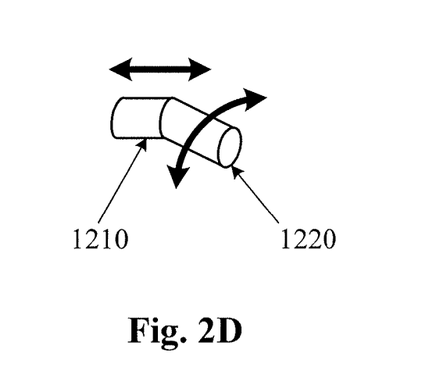

FIG. 2A is a perspective view of the distal end of a phacoemulsification hand piece according to the principles of the present invention. In FIG. 2, a phacoemulsification needle 1210 is surrounded by an irrigation sleeve 1230. The phacoemulsification needle 1210 has an open end 1220 through which lens particles are aspirated from the eye during cataract surgery. The irrigation sleeve 1230 has an optional opening 1240 through which irrigation fluid flows into the eye. The needle 1210 and sleeve 1230 are both inserted into the anterior chamber of the eye during cataract surgery. When power is applied to the hand piece, the needle 1210 vibrates ultrasonically in a longitudinal mode, a torsional mode, or in both modes simultaneously. This is more clearly seen in FIGS. 2B-2D. In FIG. 2B, needle 1210 vibrates in longitudinal mode (back and forth). In FIG. 2C, needle 1210 vibrates in torsional mode (or in a twisting or sweeping manner). In FIG. 2D, needle 1210 vibrates in both longitudinal and torsional modes simultaneously.

The two different modes (longitudinal and torsional) produce two different needle motions as shown in FIGS. 2B-2D. In general, longitudinal mode can act to cut a cataractous lens by impacting the end of the needle 1210 against the lens much like a jackhammer. Torsional mode can act to cut a lens with a side to side sweep of the end of the needle 1210. Depending on the needle geometry, the twisting motion imparted to the needle 1210 in torsional mode generally produces a side to side sweep of the end of the needle 1210. In other instances, the end of the needle 1210 sweeps in an arc. Regardless, torsional mode may be more effective in cutting a lens because it allows aspiration through open end 1220 of needle 1210 to hold the lens material on the needle 1210 for more effective cutting. In addition, in torsional mode, each sweep of the needle 1210 acts to cut the lens. In contrast, longitudinal mode produces a jack hammer motion that impacts the lens only in a forward direction (and not in a return direction). Moreover, longitudinal mode may act to repel the lens material away from the needle which may reduce cutting efficiency. However, when the open end 1220 of the needle 1210 is occluded or blocked by lens material, the repulsion effect of longitudinal mode may be effective at clearing the material which can be desirable.

When both modes are operated simultaneously, the needle 1210 moves both longitudinally and torsionally at the same time. The amount of longitudinal and torsional motion can be controlled independently as explained below. In some instances, this combination motion may be more effective at cutting the lens and/or clearing lens material from the open end 1220 of needle 1210.

Figure 3:
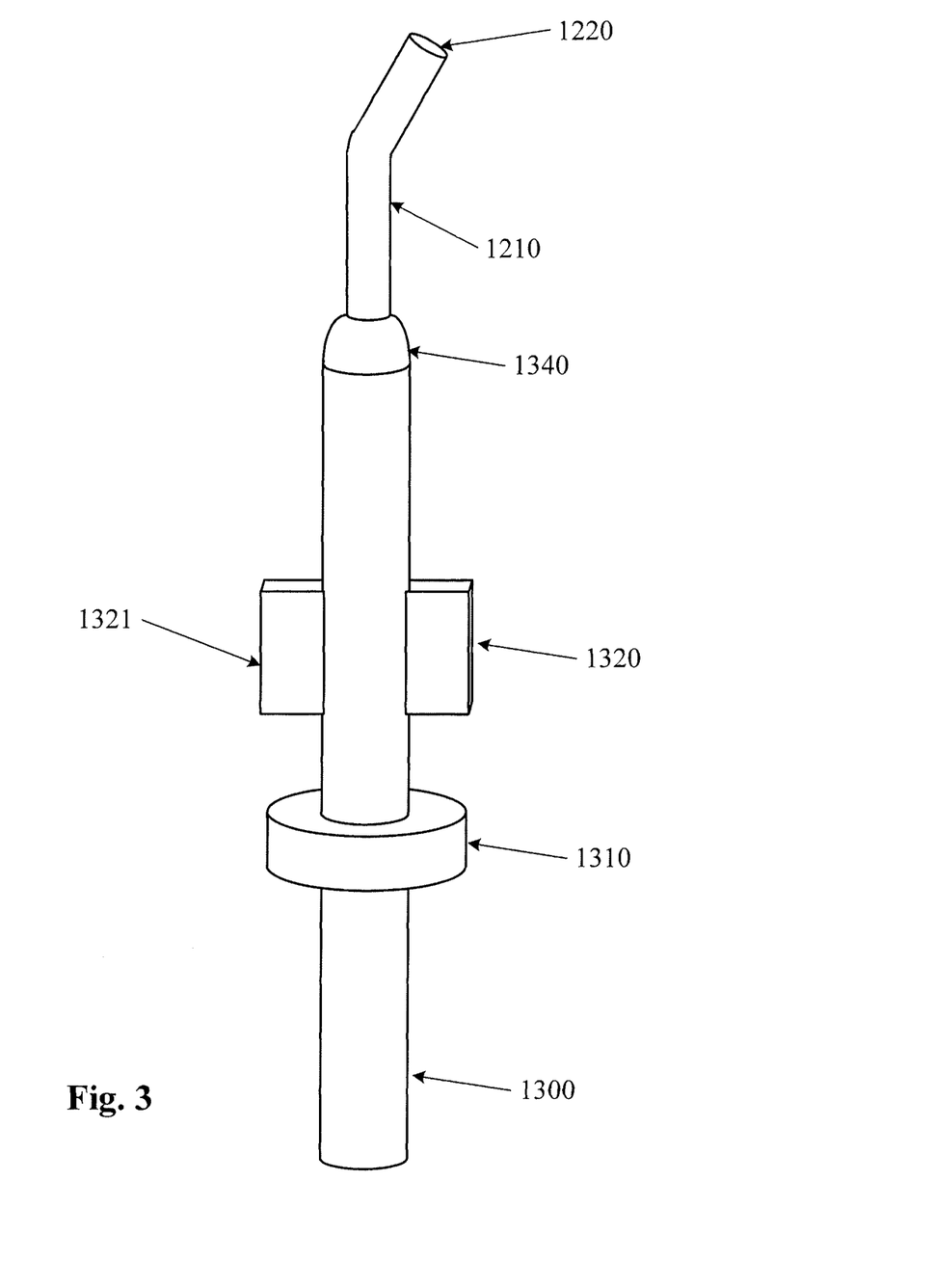
FIG. 3 is a perspective view of a horn and needle assembly according to the principles of the present invention.
Figure 4:
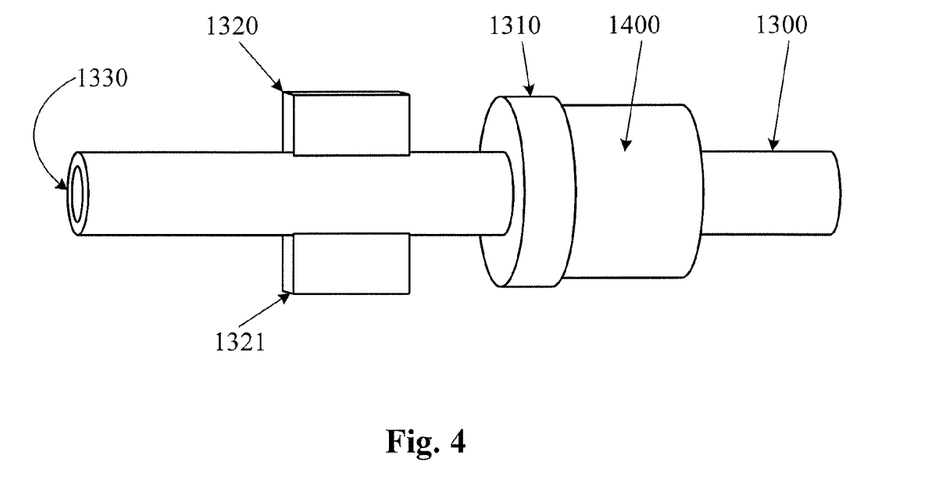
FIG. 4 is a perspective view of a horn according to the principles of the present invention.
Figure 5A:
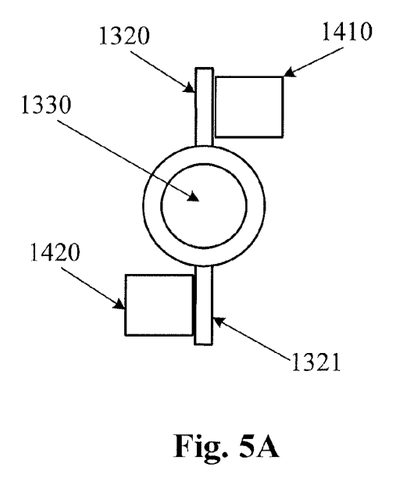
FIGS. 5A and 5B are diagrams of two embodiments of a transducer and horn according to the principles of the present invention.
Figure 5B:
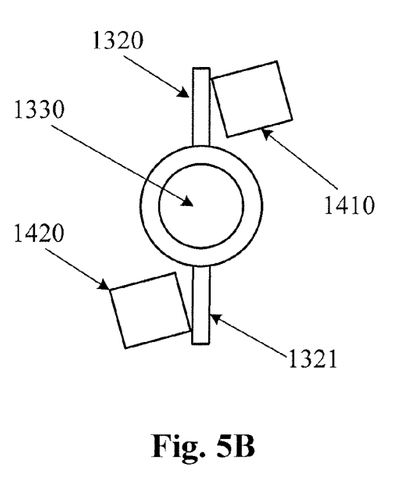

FIG. 3 is a perspective view of a horn and needle assembly according to the principles of the present invention. In FIG. 3, horn 1300 has a flange 1310, and two ears 1320 and 1321. A needle 1210 with an open end 1220 is coupled to horn 1300 via hub 1340. Needle 1210 is typically coupled to horn 1300 via a threaded connection at hub 1340. The horn 1300 is coupled to one or more transducers as shown in FIGS. 4, 5A, and 5B. Horn 1300 is typically made of a solid material such as a titanium alloy. One or more transducers produce vibrations which are imparted to horn 1300. As horn 1300 vibrates, needle 1210 also vibrates. In this manner, if horn 1300 is vibrated longitudinally, then needle 1210 also vibrates longitudinally. Likewise, if horn 1300 vibrates torsionally, then needle 1210 also vibrates torsionally.

The assembly shown in FIG. 3 is a part of a larger phacoemulsification hand piece. The horn 1300 and associated transducer(s) are held within a hand piece shell (not shown). The hand piece shell is of a form factor suitable to be held in the hand and manipulated by a surgeon during cataract surgery. As such, the shell is typically about the size of a large pencil or pen. The needle 1210 and hub 1340 typically extend from one end of the hand piece shell (not shown). In this manner, the needle 1210 (and irrigation sleeve) can be inserted into the eye and vibrated ultrasonically to fragment the lens.

Horn 1300 may be machined from a single piece of material. Flange 1310 extends radially from the horn's central body as shown in FIG. 3. In this example, flange 1310 is in the general shape of a disc, though it may be other shapes. Flange 1310 is arranged such that one or more transducers can be held against it. Likewise, ears 1320 and 1321 extend outward from the horn's central body as shown in FIG. 3. In this example, ears 1320 and 1321 are generally square or rectangular in shape, though they may be of other shapes. Ears 1320 and 1321 are arranged so that one or more transducers can be held against them.

FIG. 4 shows a horn and transducer assembly according to the principles of the present invention. In the example of FIG. 4, horn 1300 has a flange 1310 and two ears 1320 and 1321. A lumen 1330 extends through horn 1300. Aspirated lens material flows through lumen 1330. In this manner, lumen 1330 is coextensive with the internal lumen of needle 1210 (when needle 1210 is coupled to horn 1300). As such, when needle 1210 fragments lens material, that lens material can be aspirated through the internal lumen of needle 1210 and lumen 1330 of horn 1300.

Transducer 1400 is held against flange 1310 such that vibration produced by transducer 1400 results in vibration of horn 1300 (and needle 1210 when needle 1210 is coupled to horn 1300). In FIG. 4, transducer 1400 vibrates longitudinally (back and forth). Since transducer 1400 is held against flange 1310 (which is a part of horn 1300), horn 1300 also vibrates longitudinally. Consequently, a needle attached to horn 1300 would also vibrate longitudinally. In this manner, transducer 1400, when activated, operates the hand piece in longitudinal mode.

As shown in FIGS. 5A and 5B, transducers 1410 and 1420 are held against ears 1320 and 1321. Transducers 1410 and 1420 vibrate longitudinally (back and forth). Since transducers 1410 and 1420 are held against ears 1320 and 1321, horn 1300 is caused to vibrate torsionally or in a twisting or rotating manner. This torsional or twisting movement of horn is produced as the transducers 1410 and 1420 press against ears 1320 and 1321 causing a partial rotation of horn 1300. In this manner, transducers 1410 and 1420 produce vibration that is generally orthogonal to the vibration produced by transducer 1400. A needle coupled to horn 1300 would also vibrate torsionally or in a twisting fashion (i.e. in torsional mode). Typically, transducers 1400, 1410, and 1420 are piezoelectric crystals which are commonly used in ophthalmic ultrasound hand pieces.

In FIG. 5A, transducers 1410 and 1420 are held flush against ears 1320 and 1321. In FIG. 5B, transducers 1410 and 1420 are held at an angle against ears 1320 and 1321. Since transducers 1410 and 1420 vibrate longitudinally and ears 1320 and 1321 can only rotate about the central axis of horn 1300, either of these two configurations can produce sufficient torsional or twisting motion of horn 1300 and an attached needle.

To achieve torsional or twisting motion of horn 1300 and attached needle 1210, the transducers 1410 and 1420 move longitudinally to cause a rotation of ears 1320 and 1321 about the central axis of horn 1300. In FIG. 5B, the transducers 1410 and 1420 may be held at an angle equal to one half of the targeted ear rotation angle. In this way, when the transducers 1410 and 1420 move the ears 1320 and 1321 to the targeted rotation angle, the maximum angle between the transducers 1410 and 1420 and the ears 1320 and 1321 would only be one half of the targeted ear rotation angle. In contrast, in FIG. 5A, the angle between the transducers 1410 and 1420 and the ears 1320 and 1321, respectively, would be the full ear rotation angle. In this manner, the angle between the transducers 1410 and 1420 and the ears 1320 and 1321, respectively, in FIG. 5A is greater than the angle between the transducers 1410 and 1420 and the ears 1320 and 1321, respectively, in FIG. 5B. The reduced angle in FIG. 5B results in less stress on the transducers 1410 and 1420 which may prevent them from cracking.

Figure 6A:
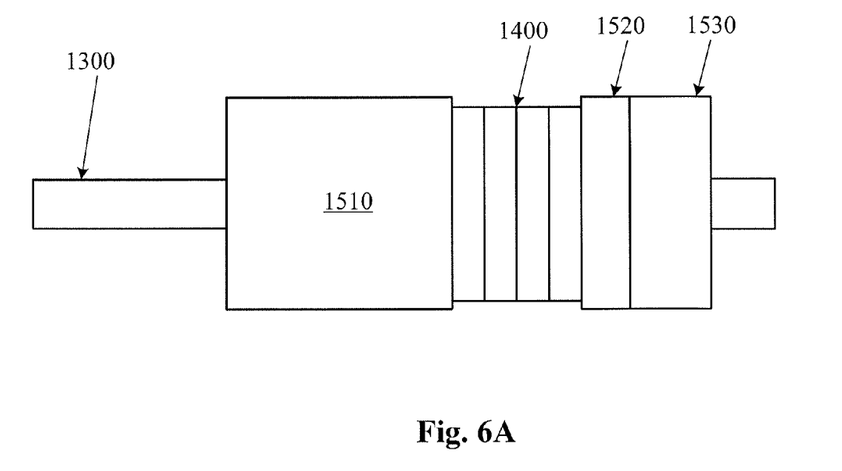
FIGS. 6A and 6B are diagrams of two embodiments of a transducer and horn according to the principles of the present invention.
Figure 6B:
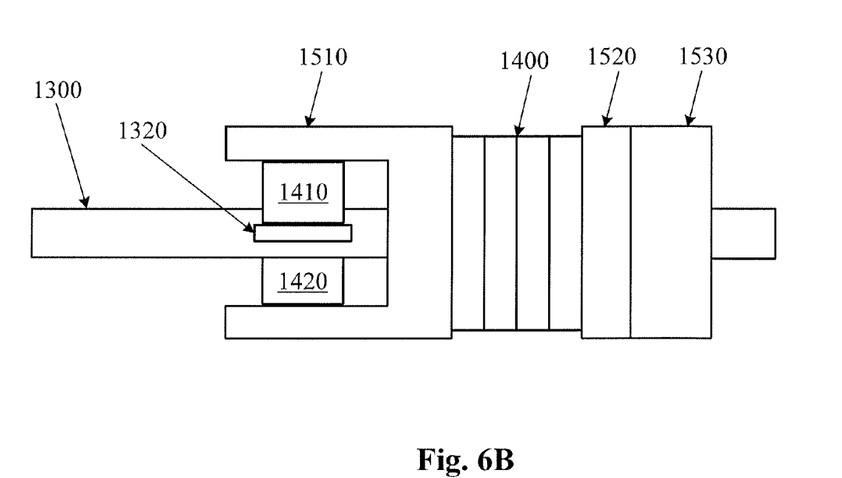

FIGS. 6A and 6B are diagrams of two embodiments of a transducer and horn according to the principles of the present invention. In FIGS. 6A and 6B, transducers 1410 and 1420 are held against ears 1320 and 1321 by a flange 1510 that is integral with or coupled to horn 1300. In FIGS. 6A and 6B, transducer 1400 is held between torque ring 1520 and flange 1510. A nut 1530 secures torque ring 1520 and transducer 1400 against flange 1510. In this manner, when transducer 1400 vibrates, horn 1300 also vibrates.

FIG. 6B shows the location of transducers 1410 and 1420. Transducer 1410 is held between flange 1510 and ear 1320. Likewise, transducer 1420 is held between flange 1510 and ear 1321 (not shown). While shown as being held flush against ear 1320, transducer 1410 may be held at an angle against ear 1320 in a manner similar to that depicted in FIG. 5B. Likewise, transducer 1420 may be held at an angle against ear 1321 in a manner similar to that depicted in FIG. 5B.

In the embodiment of FIGS. 6A and 6B, flange 1510 may be generally planar as shown or may have a radius of curvature about the central axis of horn 1300 (i.e. the axis along the lumen 1330 of horn 1300). In this example, transducers 1410 and 1420 are fitted in horn 1300. When transducers 1410 and 1420 vibrate, the vibration is localized at horn 1300. When transducer 1400 vibrates, the transducers 1410 and 1420 move with the flange 1510, ear 1320, and ear 1321.

While transducers 1400, 1410, and 1420 are shown on different figures, all three transducers may be employed in a single assembly. In this manner, all three transducers can be activated to vibrate the needle in longitudinal mode and torsional mode simultaneously. In addition, since transducers 1400, 1410, and 1420 can each be operated separately, the amount of torsional and longitudinal motion imparted to a needle can be precisely controlled. Transducers 1400, 1410, and 1420 are each typically driven by a voltage or current source. Generally, the amount of voltage (or power) applied to each transducer 1400, 1410, and 1420 determine its amplitude of vibration. The higher the voltage applied, the greater the amplitude of vibration. By controlling the voltage (or power) applied to each transducer individually, the amount of longitudinal and torsional vibration can be precisely controlled. The voltages (or power) applied to transducers 1400, 1410 and 1420 may be applied, for example, via lead wires coupled to the transducers.

For example, transducer 1400 may be driven with a low voltage that produces a small amount of longitudinal vibration in the horn 1300 and attached needle 1210. At the same time, a greater voltage can be applied to transducers 1410 and 1420 to produce a relatively large amount of torsional or twisting vibration in horn 1300 and attached needle 1210. Expressed as a percentage of maximum vibration, this example may yield 10% longitudinal vibration and 90% torsional vibration. In this manner, if all transducers 1400, 1410, and 1420 are driven at their maximum voltages, then the longitudinal vibration is 100% and the torsional vibration is also 100%. By adjusting the driving voltages for each transducer, any combination of percentages can be produced. This manner of operating the hand piece may be beneficial in that precise amounts and types of vibration can be applied to the needle 1210 to produce a desired cutting effect.

From the above, it may be appreciated that the present invention provides an improved hand piece for phacoemulsification surgery. The present invention provides a horn that is designed to impart longitudinal and torsional motion to a cutting tip simultaneously and in any proportion. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic surgical hand piece comprising:
    a horn with a central axis;
    a flange coupled to the horn, the flange having a generally flat surface, the generally flat surface of the flange extending from the horn and generally perpendicular to the central axis, the generally flat surface of the flange at least partially bounded by a surface of the horn;
    a first ear coupled to the horn, the first ear having a generally flat surface, the generally flat surface of the first ear extending from the horn such that the generally flat surface of the first ear is generally perpendicular to the generally flat surface of the flange, the generally flat surface of the first ear at least partially bounded by the horn;
    a first transducer held against the generally flat surface of the flange, such that a generally flat surface of the first transducer parallel to the generally flat surface of the flange is held against the generally flat surface of the flange; and
    a second transducer held against the generally flat surface of the first ear, such that a generally flat surface of the second transducer parallel to the generally flat surface of the ear is held against the generally flat surface of the ear.

2. The hand piece of claim 1 wherein the first and second transducers are capable of vibrating in a longitudinal direction, the first transducer imparts a longitudinal vibration to the horn, and the second transducer imparts a torsional or twisting vibration to the horn.

3. The hand piece of claim 1 further comprising:
    a second ear coupled to the horn, the second ear having a generally flat surface, the second ear extending from the horn such that the generally flat surface of the second ear is generally perpendicular to the generally flat surface of the flange.

4. The hand piece of claim 3 wherein the second ear is located generally opposite the first ear on the horn.

5. The hand piece of claim 3 further comprising:
    a third transducer held against the generally flat surface of the second ear.

6. The hand piece of claim 1 further comprising:
    a needle coupled to the horn.

7. The hand piece of claim 1 wherein driving voltages can be independently applied to the first transducer and to the second transducer.

8. The hand piece of claim 1 wherein the flange is generally disc-shaped.

9. The hand piece of claim 1 wherein the ear is generally rectangular in shape.

10. The hand piece of claim 1 wherein the horn is generally cylindrical in shape.

11. The hand piece of claim 1 wherein the horn further comprises a lumen that extends through the horn along the central axis.

12. The hand piece of claim 1 wherein the second transducer is held against the first ear at an angle.

* * * * *